(12) United States Patent
Carroll et al.

(10) Patent No.: US 8,351,038 B2
(45) Date of Patent: Jan. 8, 2013

(54) SKIN COLOR MATCHING METHOD AND SYSTEM

(76) Inventors: Charles Conrad Carroll, London (GB); Trevor Coward, London (GB)

( * ) Notice: Subject to any disclaimer, the term of this patent is extended or adjusted under 35 U.S.C. 154(b) by 904 days.

(21) Appl. No.: 11/817,536

(22) PCT Filed: Mar. 2, 2006

(86) PCT No.: PCT/GB2006/000748
§ 371 (c)(1),
(2), (4) Date: Nov. 12, 2008

(87) PCT Pub. No.: WO2006/092604
PCT Pub. Date: Sep. 8, 2006

(65) Prior Publication Data
US 2009/0213379 A1    Aug. 27, 2009

(30) Foreign Application Priority Data
Mar. 2, 2005 (GB) .................................. 0504279.1

(51) Int. Cl.
*G01J 3/46* (2006.01)
(52) U.S. Cl. ........................................................ 356/402
(58) Field of Classification Search .................. 356/402, 356/425
See application file for complete search history.

(56) References Cited

U.S. PATENT DOCUMENTS

| | | | |
|---|---|---|---|
| 5,297,555 A * | 3/1994 | Martens | 356/402 |
| 5,478,238 A * | 12/1995 | Gourtou et al. | 434/100 |
| 5,671,735 A | 9/1997 | MacFarlane et al. | |
| 6,437,866 B1 * | 8/2002 | Flynn | 356/402 |
| 6,519,038 B1 | 2/2003 | Kritchman | 356/425 |

FOREIGN PATENT DOCUMENTS

| | | |
|---|---|---|
| AU | 612899 B2 | 7/1991 |
| EP | 0 767 362 A1 | 9/1997 |
| WO | 02/102350 A2 | 12/2002 |

OTHER PUBLICATIONS

Carnelli et al., Color Realism in the Cosmetic Glove, Artificial Limbs, vol. 2, No. 2, 1955, pp. 57-65.*

(Continued)

*Primary Examiner* — Kara E Geisel
(74) *Attorney, Agent, or Firm* — Heslin Rothenberg Farley & Mesiti P.C.

(57) ABSTRACT

A first method for matching skin colors comprises measuring a spectral reflectance curve of an area of skin and determining a blend of pigments to match the skin's color by combining spectral reflectance curves measured for pigments to produce a calculated spectral reflectance curve corresponding to that of the skin. The pigment blend is then used, for example, to pigment a medical prosthesis, so that it matches precisely its wearer's skin. This method avoids the problem of metamerism in which colors that match under a first illumination no longer match under a second illumination. A second method uses a database of pigment blends generated by the first method. The color of an area of skin is measured and a pigment blend is selected from the database that provides a closest match. Apparatus for carrying out such color matching is also provided, together with palettes of suitable pigments for skin color matching.

35 Claims, 1 Drawing Sheet

OTHER PUBLICATIONS

Figure 1:
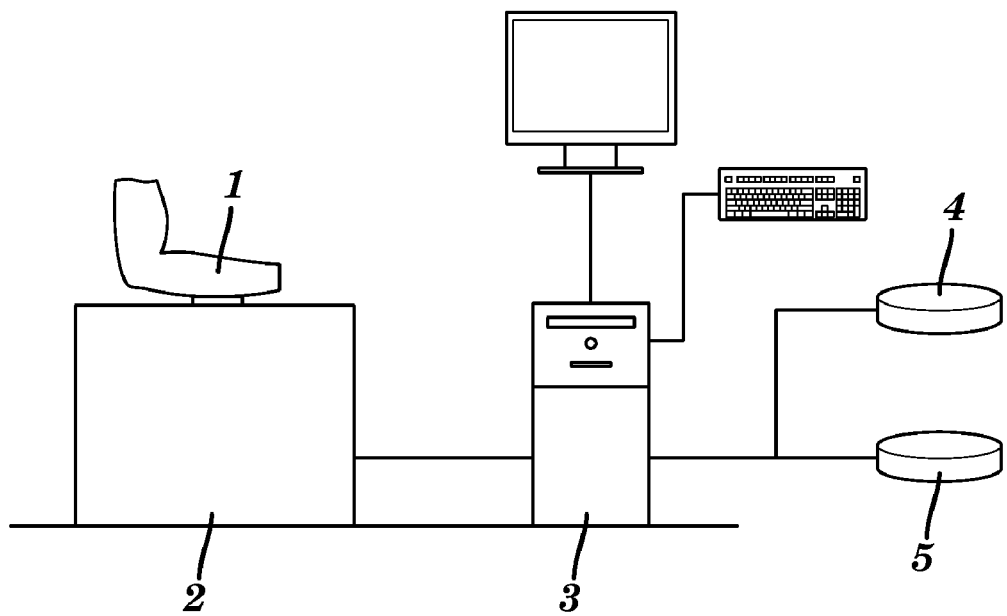

Koran et al., Material Science: Reflection Spectrophotometry of Facial Skin, Journal of Dental Research, vol. 60, No. 6, Jun. 1981, pp. 979-982.*

Cantor et a l., Methods for evaluating prosthetic facial materials, Journal of Prosthetic Dentistry ,vol. 21, No. 3, Mar. 1969, pp. 324-332. 1969.*

Angelopoulo E et al., "Multispectral skin color modeling", Proceedings 2001 IEEE Conference on Computer Vision and Pattern Recognition, CVPR 2001, Dec. 8-14, 2001, vol. 1 of 2, pp. 635-642, XP010584184, ISBN 0-7695-1272-0.

* cited by examiner

SKIN COLOR MATCHING METHOD AND SYSTEM

CROSS-REFERENCE TO RELATED APPLICATIONS

This application is a Section 371 filing of International Application PCT/GB2006/000748 filed Mar. 2, 2006 and published, in English, as International Publication WO 2006/092604 A2 on Sep. 8, 2006, which claims priority of Great Britain application no. 0504279.1 filed on Mar. 2, 2005, all of which applications are hereby incorporated herein by reference, in their entirety.

BACKGROUND ART

The present invention relates to a method for accurately matching skin colors under diverse illumination conditions, and to equipment for carrying out such a procedure. More particularly, but not exclusively, it relates to a method and associated equipment for matching the appearance of a prosthesis to a natural skin tone of a user.

Systematic color matching methods are known from many fields, such as paint formulation and plastics pigmentation. Generally speaking, a device such as a colorimeter is used to measure a color of a sample, and a pigment or pigments are selected to produce substantially the same color in the dry paint, compounded polymer, and so forth.

Any color can be defined in terms of three independent co-ordinates, and several alternative co-ordinate systems are in use. Probably the most commonly used is the CIE L*a*b* system, in which a color is assigned a brightness value (L*), a value on a red-green axis (a*) and a value on a blue-yellow axis (b*). An alternative is the CIE L*c*h° system, in which a color is described using a brightness value (L*), a chroma value (c*—in general terms, an intensity of color) and a hue angle (h°—in general terms, which color it is—yellow, orange, purple and so forth).

For color matching in the CIEL*a*b* system, an overall measure of color difference $\Delta E^*$ is calculated from the individual differences in the three coordinates, $\Delta L^*$, $\Delta a^*$ and $\Delta b^*$, according to the formula:

$$\Delta E^* = \sqrt{[(\Delta L^*)^2 + (\Delta a^*)^2 + (\Delta b^*)^2]}$$

A skilled color matcher may be able to distinguish between two samples having a $\Delta E^*$ of around 0.5. For most practical purposes, a $\Delta E^*$ of 1.0 or below may be considered a visual match. A corresponding overall measure of color difference may be calculated from the respective CIEL*c*h° coordinates, allowing use of the CMC color tolerance system, developed by the Color Measurement Committee of the Society of Dyers and Colorists. This uses a weighted formula which has been found to correlate with results from human color matchers slightly better than the simple $\Delta E^*$ formula, above. A further color difference measure may be calculated by following the CIE94 system, developed by the Commission Internationale de l'Eclairage. This, too, incorporates weighting factors to produce a better correlation with human results. The CMC and CIE94 color differences should each be 1.0 or below for a match.

Such single point measurements are however not always sufficient. A standard colorimeter is a tristimulus device, making measurements at three wavelengths only (generally a "red", a "green" and a "blue" wavelength), which are mathematically converted into L*a*b* values or other co-ordinate system of choice.

However, the appearance of a surface in practice depends on the illumination under which it is viewed. Paint color matching is conventionally performed under a standard "north light", equivalent to north-facing daylight at noon, and a paint colorimeter is hence adapted to simulate this standard illuminant. There are other standard illuminants, for example corresponding generally to incandescent lighting and to fluorescent lighting. A color match produced under a given standard illuminant will only be strictly valid under that illuminant, and not necessarily under others.

The effect whereby two surfaces appear to have the same color under some illumination conditions, but are visibly different under others, is known as metamerism. This is caused by differences in how pigments absorb and reflect light across the whole visible spectrum. Thus, the curves for two pigments (or pigment blends) may differ in a particular wavelength range but be similar elsewhere. Viewed under an illuminant with a low intensity in this wavelength range, the two pigments will appear the same, but under an illuminant with a significant intensity in this range, they will appear substantially different. This effect cannot be measured by a simple tristimulus colorimeter or the like, nor characterised by a small number of coordinate values.

Metamerism is a particular problem when matching skin tones, and especially when matching a prosthetic device to a skin tone of its wearer. While artificial limbs and the like are now available that comprise a silicone plastics material approximating to the wearer's skin color, these are only matched under a standard illuminant, and any visual checking is likely to take place under artificial lighting. The human visual system is particularly sensitised to differences in skin tones, so even small metameric effects will be noticed. A prosthesis that is clearly a prosthesis, for example because it does not match the wearer's skin tone in daylight, is not fully acceptable to the wearer.

As a result, technicians performing color matches for prosthetics have not widely adopted color measurement techniques, and many continue to trust to their experience and mix pigments "by eye". However, this may require a lengthy process of trial and error, and fails to address the problem of metamerism.

While this problem is significant with pale, Caucasian skin tones, it is believed to be even greater with darker skins, particularly Asian and Afro-Caribbean skin colors. Even experienced technicians can have problems making an initial match to non-Caucasian skin tones, even before issues of metamerism arise. As well as conventional prostheses, camouflaging treatments to conceal the effects of skin conditions such as vitiligo will be more important for darker skin tones.

It is hence an object of the present invention to provide a method for matching skin colors, particularly for prostheses and other medical applications, that obviates the problems with metamerism referred to above and permits more rapid and accurate pigment blend formulation than hitherto. It is also an object of the present invention to provide apparatus for carrying out the above method, and to provide palettes of selected pigments for matching skin colors, including non-Caucasian skin colors.

BRIEF SUMMARY OF THE INVENTION

According to a first aspect of the present invention, there is provided a method for matching a selected skin color comprising the steps of providing a color measurement device adapted to measure a first spectral reflectance curve of an area of skin to be matched, providing a colorant database containing colorant spectral reflectance curves for a plurality of colorants, measuring a first spectral reflectance curve for a selected area of skin, comparing said first spectral reflectance curve to said colorant spectral reflectance curves and determining a recommended blend of colorants chosen from the colorant database, said recommended blend having a calculated spectral reflectance curve substantially corresponding to that measured for the selected area of skin.

Preferably, the method comprises the further steps of preparing a sample of said recommended colorant blend in an application medium, measuring the spectral reflectance curve of the sample and comparing the curves of the sample and the selected area of skin in order to check the match.

Advantageously, the method comprises the step of making a visual check of the resemblance of the sample to the selected area of skin.

Preferably, the method also comprises the step of measuring tristimulus color values for the selected area of skin.

Advantageously, the method then comprises the step of calculating CIE L*a*b* and/or CIE L*c*h° color values for the selected area of skin.

The method may then comprise the steps of calculating color differences, such as ΔE*, between the selected area of skin and proposed blends of colorants and rejecting blends for which the color difference exceeds a preselected threshold value.

The method preferably comprises the additional step of recording in a formulation database means a recommended blend of colorants found to constitute a successful match, together with its respective spectral reflectance curves and color values.

Preferably, the method also comprises the step of providing a palette of colorants corresponding to selected ones of colorants present in the colorant database.

Advantageously, each colorant in the palette is provided as a premix, dispersion, masterbatch, concentrate or the like, adapted to be readily mixable into the application medium.

According to a second aspect of the present invention, there is provided a method for matching a selected skin color comprising the steps of providing a color measurement device adapted to measure color data of an area of skin to be matched, providing formulation database means containing a plurality of blends of colorants that have previously been found to match skin colors by the method described in the first aspect above, along with their respective color data, measuring color data for a selected area of skin and selecting a recommended blend of colorants from the formulation database means which has calculated color data closest to the color data measured for the selected area of skin.

In a first embodiment of the method, said color data comprise tristimulus color values The tristimulus color values may be expressed according to the CIE L*a*b* and/or CIE L*c*h° systems.

The colorant blend selection step may then comprise calculating color differences between calculated color data for blends of colorants and measured color data for the selected area of skin, according to the ΔE*, CMC and/or CIE94 formulae.

The method may optionally comprise the additional steps of providing a color measurement device adapted to measure spectral reflectance curves, measuring spectral reflectance curves for the sample and the selected area of skin, and comparing said curves, for example to confirm the absence of metamerism.

In a second embodiment of the method, the color data comprise spectral reflectance curves.

The method may then optionally comprise the step of calculating tristimulus color values from the spectral reflectance curves.

In either embodiment, the method preferably comprises the further step of assessing a difference between the color data calculated for the recommended blend of colorants and measured for the selected area of skin against a predetermined threshold value.

Advantageously, when said difference exceeds the threshold value, the method further comprises the step of modifying the recommended blend of colorants to reduce said difference below the threshold value.

Said modification step may comprise providing a colorant database comprising colorant spectral reflectance curves for a plurality of colorants and so modifying the recommended blend of colorants using colorants selected from the colorant database that it has a calculated spectral reflectance curve substantially corresponding to that measured for the selected area of skin.

Preferably, the method comprises the further steps of preparing a sample of said recommended colorant blend in an application medium, measuring the color data of the sample and comparing them with those of the selected area of skin.

Advantageously, the method comprises the step of making a visual check of the resemblance of the sample to the selected area of skin.

Preferably, the method also comprises the step of providing a palette of colorants corresponding to colorants used in the colorant blends present in the formulation database means.

In each of the first and second aspects, above, the application medium may be a material suitable for the production of prostheses.

Said material may comprise a plastics material, optionally a silicone polymer, a polyurethane polymer or a rubber latex composition.

Alternatively, the application medium may be a composition adapted to camouflage a skin condition such as vitiligo or a birthmark.

The application medium may instead comprise a surface coating composition.

According to a third aspect of the present invention, there is provided apparatus for matching skin color, comprising a color measurement device adapted to measure a first spectral reflectance curve for a selected area of skin and operatively linked to a first computer, the first computer being connected to a colorant database containing reference spectral reflectance curves for a plurality of colorants, wherein the computer is programmed to determine a recommended blend of colorants by combining colorant reference spectral reflectance curves substantially to match a first spectral reflectance curve of the selected area of skin.

Preferably, the apparatus also comprises a plurality of samples of colorants corresponding to selected ones of those present in the colorant database.

The colorant database may comprise a database held remotely on a second computer, connectable to the first computer.

Alternatively, the colorant database may comprise a database held on the first computer, optionally on a removable data carrier means insertable into the first computer.

According to a fourth aspect of the present invention, there is provided apparatus for matching skin color, comprising a color measurement device adapted to measure color data for a selected area of skin and operatively linked to a first computer, the first computer being connected to a formulation database containing a plurality of blends of colorants that have previously been found to match skin colors by the method described in the first aspect above, along with their respective color data, wherein the computer is programmed to select a recommended blend of colorants from the formulation database which has calculated color data closest to the color data measured for the selected area of skin.

Preferably, said color data comprise spectral reflectance curves.

Alternatively or additionally, said color data may comprise tristimulus color values.

The apparatus may also comprise a plurality of samples of colorants corresponding to those present in the blends of colorants present in the formulation database means.

The formulation database means may comprise a database held remotely on a second computer, connectable to the first computer.

Alternatively, the formulation database means may comprise a database held on the first computer.

Optionally, the formulation database means comprises a first database held on the first computer and a second database held on a second remote computer, the first database comprising selected ones of the blends of colorants present in the second database.

According to a fifth aspect of the present invention, there is provided a palette of pigments for use in matching skin colors, comprising a white pigment, a first substantially yellow pigment, a first substantially red pigment, a cold-toned pigment and at least one balancing pigment.

Preferably, said first substantially yellow pigment comprises a substantially mid-shade yellow pigment, such as Pigment Yellow 93 (Color Index 20170), quinoline yellow (Color Index 47005), Pigment Yellow 1 (Color Index 11680), arylide yellow (Pigment Yellow 3; Color Index 11710), Pigment Yellow 128 (Color Index 20037) and Pigment Yellow 180 (Color Index 21290).

Advantageously, said white pigment comprises a high-refractive index pigment such as titanium dioxide or zinc oxide.

The first substantially red pigment may comprise a dark and/or blue-shade red pigment, such as quinacridone magenta (Pigment Red 122; Color Index 73915), deep maroon (Pigment Red 63; Color Index 15880), perylene maroon (Pigment Red 179; Color Index 71130) D&C Red 7 (Color Index 15850:1), D&C Red 33 (Color Index 17200), or manganese violet (Color Index 77742).

The cold-toned pigment may comprise a green, blue, black or violet pigment.

Said green pigment may comprise chromium oxide green (Color Index 77283), viridian (hydrated chromium oxide green; Color Index 77289) or phthalocyanine green (Color Index 74265).

Said blue pigment may comprise ultramarine blue (Color Index 77007), phthalocyanine blue (Color Index 74160) or Prussian blue (Color Index 77510).

The balancing pigment may comprise an iron oxide pigment such as Mars yellow (Color index 77492), Mars red (Color Index 77491), maroon red (Color Index 77491), iron oxide oranges and browns (Color Index 77491 and 77492), iron oxide violet (Color Index 77105) or iron oxide black (Color Index 77499).

The balancing pigment may alternatively or additionally comprise a dark red pigment, such as perylene maroon (Color Index 71130) or D&C Red 40 (Color Index 16035).

The balancing pigment may alternatively or additionally comprise an ultramarine pigment, such as ultramarine pink or ultramarine blue (both Color Index 77007).

The palette of pigments may be particularly adapted for matching pale Caucasian skin tones, and then comprises titanium dioxide; a mid-shade yellow pigment, particularly Pigment Yellow 93; a blue-shade red pigment, particularly quinacridone magenta; a cold-toned pigment selected from ultramarine blue, phthalocyanine blue, viridian, phthalocyanine green, a black pigment and manganese violet; and as balancing pigment either an iron oxide pigment or ultramarine pink.

The palette of pigments may be particularly adapted for matching dark Caucasian skin tones, and then comprises titanium dioxide; a mid-shade yellow pigment, particularly Pigment Yellow 93; a blue-shade red pigment, particularly quinacridone magenta; a cold-toned pigment selected from ultramarine blue, phthalocyanine blue, chromium oxide green and viridian; and as balancing pigment either an iron oxide pigment, ultramarine pink or a dark red pigment.

The palette of pigments may be particularly adapted for matching pale Asian skin tones, and then comprises titanium dioxide; a mid-shade yellow pigment, particularly Pigment Yellow 93; a dark red pigment, particularly perylene maroon; a cold-toned pigment selected from ultramarine blue, phthalocyanine blue, a black pigment, viridian and phthalocyanine green; and as balancing pigment either an iron oxide pigment or ultramarine pink.

The palette of pigments may be particularly adapted for matching dark Asian skin tones, and then comprises titanium dioxide; a mid-shade yellow pigment, particularly Pigment Yellow 93; a blue-shade red pigment, particularly quinacridone magenta or manganese violet; a cold-toned pigment selected from ultramarine blue, phthalocyanine blue, a black pigment, viridian and phthalocyanine green; and as balancing pigment either an iron oxide pigment, ultramarine pink or a dark red pigment.

The palette of pigments may be particularly adapted for matching lighter Afro-Caribbean skin tones, and then comprises titanium dioxide; a mid-shade yellow pigment, particularly Pigment Yellow 93; a dark or blue-shade red, such as perylene maroon, deep maroon or manganese violet; a cold-toned pigment selected from ultramarine blue, phthalocyanine blue, a black pigment, viridian and phthalocyanine green; and as balancing pigment either an iron oxide pigment or ultramarine pink.

The palette of pigments may be particularly adapted for matching darker Afro-Caribbean skin tones, and then comprises titanium dioxide; a mid-shade yellow pigment, particularly Pigment Yellow 93; a dark or blue-shade red pigment, such as perylene maroon or manganese violet; a cold-toned pigment selected from ultramarine blue, phthalocyanine blue, a black pigment, viridian and chromium oxide green; and as balancing pigment either an iron oxide pigment or ultramarine blue.

In each case, the pigments of the palette may be provided as concentrates, masterbatches, premixes, dispersions or the like, prepared for ease of incorporation into a predetermined application medium.

Said application medium may comprise a plastics material suitable for the production of prostheses, such as a silicone polymer, a polyurethane material or a latex rubber material.

Alternatively, the application medium may comprise a composition adapted to camouflage a skin conditions such as vitiligo or a birthmark.

According to a sixth aspect of the present invention, there is provided a prosthesis comprising material pigmented by a method as described in the first or second aspects above.

According to a seventh aspect of the present application, there is provided a prosthesis comprising pigments as described in the fifth aspect above.

According to an eighth aspect of the present invention, there is provided a skin condition camouflage composition comprising material pigmented by a method as described in the first or second aspects above.

BRIEF DESCRIPTION OF DRAWING FIGURES

Figure 2:
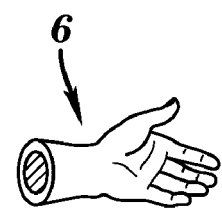

Embodiments of the present invention will now be more particularly described by Way of example with reference to the accompanying drawings in which:

FIG. 1 is a schematic depiction of apparatus for skin color matching according to the present invention; and FIG. 2 depicts a prosthesis that may be colored according to the present invention.

In a first skin color matching method embodying the present invention, an area of a subject's skin 1 is selected for measurement, taking care to avoid veins, blemishes and other marks. Where possible, an area of skin is chosen to correspond to that to be simulated by a prosthesis—for example a subject's left arm when a right arm prosthesis is to be produced.

Occasionally, another part of the body may have to stand proxy for the part to be matched; for example, the inside of the arm may be measured in place of the ear, which may be difficult to measure. It is also possible to consider matters such as tanning, and where appropriate to produce a "summer" prosthesis for areas such as the face or outside of the arm that may tan significantly.

The area of skin to be measured is cleaned carefully, and allowed to settle to a normal color. The ambient temperature should be in a normal range to avoid color changes such as flushing, and direct skin contact should be kept to a minimum to avoid blenching.

A color measurement device 2 is used which is capable of measuring a reflected light value at a plurality of points across at least the visible spectrum (although matching is possible based on results for less than the entire visible spectrum—see below). Spectrophotometers or spectrodensitometers with this capability are readily available. The preferred device is a spectrophotometer using sphere based measurement geometry. A spectrophotometer using the alternative "45 degree" geometry may suffer from a small systematic shift in the color measured, believed to be due to the slight translucency of skin. Spectrodensitometers may suffer from similar problems.

Preferred devices are those with a hand-held measurement head that can be presented to exactly the selected area of the subject's skin. Either a single measurement is taken, or a series of measurements on the same or different skin areas can be combined, if preferred.

The spectrophotometer or other device (or an associated computer) then converts its measurements into a graph of reflected light intensity against wavelength. The measurements at preselected wavelengths are also converted into CIE L*a*b* and CIE L*c*h° coordinates.

A simple color match may then be made by selecting a combination of pigments from a library database, that should give a $\Delta E^*$ value (or the equivalent in the CMC or C1E94 systems) of less than one. However, this would not take account of potential metamerism.

Therefore, a computer program in a computer 3 is used to select a combination of pigments that gives a close match to the measured reflectance curve across substantially the whole visible range. To permit this, a sizable "palette" of pigments is first created by measuring the full spectral reflectance curves of each pigment incorporated into the prosthesis material at known concentrations, and recording the curves in a palette or colorant database 4. NB: although the visible spectrum is usually considered to extend from 400 to 700 nm in wavelength, the human eye is markedly less sensitive to wavelengths at the extremes of the range. It has been found that it is only necessary to measure and compare reflectance curves between 420 and 680 nm.

A large number of pigments have been measured, although it has been found that a vast majority of skin tones may be matched with only a small pigment palette (see below). A palette of only five pigments (one being white) has been found to suffice for most Caucasian skin tones. A set of eleven core pigments will be sufficient for most of the skin tones, of all types, measured to date, and with the substitution of a few alternatives to the core pigments, almost all skin tones can be simulated. The full palette database will require more than these pigments in order to handle special cases, however.

The computer will thus present a user with a recommended formulation that should simulate the subject's skin color to the naked eye under all lighting conditions. This formulation may be expressed as parts by weight or by volume as preferred.

The user then formulates a sample of prosthesis material, such as a silicone composition, a polyurethane composition or a latex rubber composition, using premixed concentrates of each pigment. This sample is then measured by the same procedure as was the subject's skin, ideally having a color difference value of less than one by both the CMC and the CIE94 systems (although one or the other may suffice). Finally the user compares the sample to the subject's skin by eye.

Rarely, a sample made according to the recommended formulation will not match sufficiently accurately (for example, the recommended pigments might interact when mixed, and not give exactly the color expected). In this case, the software is requested to produce an alternative formulation, compensating for the measured discrepancy, and a fresh sample is made up and checked.

Once a match has been achieved, the prosthesis 6 may be made up, using the recommended pigment formulation, and should be so similar in appearance to the subject's skin as to be unnoticeable to casual observation under all conditions of illumination.

In practice, a prosthesis will also need to be matched for opacity and surface mattness or gloss. However, it is found that these can be dealt with out significant effects on the color matching process, above.

A corresponding procedure employing the same principles is used to produce skin condition camouflage compositions to, match particular subject skin colors.

In a preferred embodiment, each successful pigment blend is recorded in a formulation database 5, together with its corresponding spectral reflective curve, and CIE L*a*b* and CIE L*c*h° values. Ideally, such data will be passed to a centralized formulation database, for example via electronic mail or the Internet. Information can this be built up on pigment blends providing substantially metamerism-free matches to an extensive range of skin tones.

A second skin color matching method embodying the invention is usable by colorists who have access only to tristimulus colorimeters and the like, rather than the more expensive spectrophotometers, etc, required for the first method, above.

The second method requires the use of a formulation database such as that described above, containing pigment blends that have provided substantially metamerism-free matches to a range of skin tones. It is envisaged that access to such a database would be via a secure Internet website or by providing a database on a CD-ROM or the like, with regular updates.

A skin area of a subject to be matched is selected and measured as described for the first method, above.

Where the colorist has access to a spectrophotometer or equivalent, a full spectral reflectance curve and CIE L*a*b*/CIE L*c*h° readings are taken. The reflectance curve is compared with the database of curves for successful non-metameric blends, and a closes; match is selected. In almost all cases, this will have a $\Delta E^*$ value (or equivalent) of less than one, so should be a visual match for the subject's skin.

The software provided with the database asks the colorist for further information concerning the system to be pigmented. For a prosthesis, a base material may be specified, along with a thickness of that material to be used, and the amount of flocking or other matting agent to be added. A base material must be specified, since a pigment blend optimised for a silicone polymer may not give exactly the same results in another polymer system, owing to differences in pigment dispersibility in different media. The thickness will govern the opacity required from the formulation.

Similarly, for a camouflage application (e.g. to mask birthmarks, scars, vitiligo and other skin conditions, or to blend in edges of a prosthesis), one may specify the type of composition and the pigment carrier involved, the density of coverage required, and so forth. The software will then produce a recommended formulation to match the measured skin color.

The recommended formulation is then mixed by the colorist to produce a test sample, which is remeasured and checked visually to confirm that it is a true match.

If the database contains no sufficiently-close matches for the particular skin tone measured, the colorist may submit the measured reflectance curve and CIE L*a*b*/CIE L*c*h° values to another colorist (e.g. acting as a consultant), who has the facilities to carry out the first method above, and will provide a bespoke formulation for that particular skin tone, (This will be added to the formulation database once its accuracy in practice is confirmed).

Where the colorist is only able to measure CIE L*a*b* values, using a tristimulus device, the L*, a* and b* values are compared with corresponding values recorded in the database of successful formulations. One or more pigment blends for which $\Delta E^*$ should be less than one are then recommended by the software.

Where only CIE L*a*b* data is available, the recommended formulation(s) from the database cannot be guaranteed to be full metameric matches, although experience has already shown that is it highly likely. This can be checked when the formulations are made up as test samples.

In rare situations, the database may not contain a formulation that is a sufficiently close match, or the recommended formulations may show visible metamerism when made up. The subject will then have to be referred to a consultant colorist who has the equipment required to make up a bespoke matching formulation, using the first method, above. (When successful, this bespoke formulation will of course be added to the next update of the database).

A third skin color matching method has similarities to be the second method, above, in that it uses a database of existing color-matched metamerism-free formulations. However, it involves the measurement of full spectral reflectance curves, thus requiring access to a spectrophotometer or the like, not just a colorimeter.

In this method, the formulation database is maintained on a central computer, remotely accessible to authorised users over the Internet or the like. The central computer also holds a database of pigment spectral reflectance curves, together with formulation software which is capable of selecting a combination of pigments to match a measured spectral reflectance curve (corresponding to the palette database and the computer program used to create formulations from scratch, described in the first method above). The user of the method is provided with software allowing remote access to the central databases and the formulation software, and does not hold the full formulation software on his or her own local computer.

The user measures a spectral reflectance curve of an appropriate region of a subject's skin, and transmits this to the central computer. Here, it is compared to existing formulations from the formulation database, and an existing formulation that is closest in color is selected.

Alternatively, the user is provided with a restricted formulation database comprising a selection of more frequently used existing formulations. In this case, the measured skin spectral reflectance curve is compared to the restricted formulation database on the user's own local computer.

In either case, the closest formulation found may be sufficiently close in color to be used. However, it is quite possible, particularly using the restricted database, that the measured skin color and that previously determined for the closest formulation would differ by more than a permissible amount (e.g. $\Delta E^*$ of 1 or more).

If this occurs, the measured skin spectral reflectance curve and the closest formulations are transmitted to the central computer, where they are fed into the full formulation software. The full formulation software works on an iterative basis, making a series of predictions of matching formulations, each a modified version of its predecessor, until it achieves a sufficiently close match to a measured skin spectral reflectance curve. The closest formulation from the formulation database may thus be fed into the full formulation software as if it were such a prediction, and the formulation software will optimise it until a match is achieved. In practice, only one iteration is normally required to modify the closest formulation from the formulation database to produce a sufficiently close match (for example, where there is a $\Delta E^*$ of 2.5 or less between the closest formulation and the measured skin reflectance curve, a single iteration of the full formulation software will almost always reduce $\Delta E^*$ to less than 0.6, i.e. practically invisible to the untrained eye).

The optimized formulation will then be sent back to the user to be made up, double-checked by machine and/or by eye and used in making a prosthesis.

Meanwhile, the optimized formulation may be added to the formulation database for future use. Optionally, the optimized formulation will be verified and re-checked before it is entered into the database (for radically different formulations, it may be preferable to check them for scratch using the first method, above). However, where the optimized formulation is a simple interpolation, close to one already present in the formulation database, it may if desired be added without prior verification.

Thus, the formulation database will grow steadily with use. Users who have remote access to the full database will thus have an even greater chance of finding a ready-made formulation to match a subject's skin tone. The restricted formulation databases supplied for local use may also be updated if a new formulation turns out to be particularly widely useful.

The three methods described above have differing hardware requirements, and the choice of which to use may depend on the availability of color measuring devices within a user's budget. It is also envisaged that the differing degrees of database and software access would incur differing license costs.

The database of matched skin tones can be improved and extended by taking a plurality of reflectance curve measurements from each subject, not only those required for the prosthesis to be produced. Similarly, skin tone readings from volunteer subjects may be made and matched, purely for the purpose of building up as broad a coverage as possible (for example, where a particular skin color is relatively uncommon and seldom requires matching—e.g. when a relatively small ethnic grouping is involved, such as Amerindians).

The database may be classified by ethnicity to speed matching.

As noted above, the ease of accuracy of color-matching may depend to a significant extent on the instruments used for color measurement. The preferred device is a spectrophotometer using spherical measurement geometry, rather than a spectrophotometer using the alternative "45-degree" measurement geometry, or a spectrodensitometer, both of which may suffer from a small systematic error when measuring skin color. This error would be correctable in practice, but would add a step to the procedure. Such errors lessen with the use of larger measuring apertures, and repeatability also improves as a larger area is measured. While larger apertures may have practical drawbacks, a measuring aperture of 8 to 15 millimeters in diameter currently appears optimal.

Non-contact color measurement methods are preferred, to avoid color changing due to skin blenching on contact with a measurement device. Digital image capture technology is being developed that will allow a full spectral width reflectance curve to be produced without skin contact. At present the technology is in its infancy and such equipment is far more expensive than commercial spectrophotometers, and is not yet available in portable form. However, it is envisaged that such equipment would be well suited to the methods described herein when it become more freely available.

LED-based equipment is known, which illuminates a substrate (e.g. skin) with light produced from various combinations of LEDs having different colors, and derives spectral information from the light reflected in each case. Again, this equipment has not been yet developed into a form usable in the present invention, but it is likely to become well-suited in due course.

Colorimeters are cheaper than the devices mentioned above, but since they measure only tristimulus values and not a substantially full spectral curve, they can only be used in the method above based on a database of existing formulations, and not for formulating from scratch. As is the case for spectrophotometers, a sphere-based measurement geometry is found to be the most reliable and to correspond best to what is seen by the naked eye.

The possible systematic error mentioned above results from the translucency of skin and subcutaneous tissues. Most color measurement techniques assume that the sample being tested is wholly opaque and only light reflectance/scattering from its surface is occurring. However, when skin is being measured, some light will pass through the skin into subcutaneous tissue. Part of this light will be absorbed, while a remainder will emerge in unpredictable directions (which might not be picked up by restricted measurement geometry devices, such as 45-degree geometry). The net result is that the measured skin color may be bluer and darker than it should be, and may well require subsequent correction.

A new type of measuring device known as a translucency meter has recently teen developed, which can assess how much light is being scattered or lost within a translucent sample. This would enable a compensation or correction factor to be added. Unfortunately, such devices cannot be used on thinner, highly opaque samples such as paints or cosmetics.

Translucency is also an issue when samples of prosthesis material are made up and tested to check the accuracy of a color-match. These are usually slightly translucent, particularly for paler skin shades. One problem that may arise is that some of the incident light may escape from the sides of the sample when color measurements are being taken. To obviate this problem, the sample can be sized to fit into the measuring aperture of the spectrophotometer or other measuring device.

Another consideration arising from the slight translucency of the prosthesis material is that conventional color measurement techniques rely on the sample measured being wholly opaque—i.e. no light passes through the sample. The normal measure of opacity is contrast ratio (CR). A CR of 100% represents total opacity, but in practice a CR of 99.9% is sufficiently close. Opacity increases with sample thickness, but some colors are more opaque than others (for example, at a given sample thickness, a light color will usually have a lower CR than a dark color). It is hence normal to prepare samples having a thickness so great that all colors give a CR of at least 99.9%; for prosthesis material, samples six millimeters thick are standard.

However, the polymer layer on a prosthesis may be only one or two millimeters thick. Darker skin tones may well produce a CR of 99.9% at this thickness, completely obscuring the internal structure of the prosthesis. However, paler skin tones may well have lower CRs at this thickness, so the internal structure of the prosthesis might be slightly visible. Thus, paler skin tones may require adjustments to be made to the "matched" formulation, to increase its opacity. For skin condition camouflage compositions, applied thicknesses are much lower, and so the correction of colors measured on skin becomes even more important.

As the centralized formulation database is built up, it can also record the thicknesses to which matches were formulated; ultimately, it will enable interpolation so that a predicted matching formulation should both have the correct color and a sufficiently high CR at the application thickness which is to be used.

While the above methods have been described in terms of color matching for prostheses or broadly medical skin camouflaging uses, it is envisaged that the same approach might be of use in other applications.

In some cases, a prosthesis may be painted, powder-coated or otherwise surface-coated, instead of covered with layers of silicone polymer or the like. The above method can easily be extended to provide surface coating compositions that when dry or cured will match a subject's skin under all illuminations.

A further application in which such a database of natural skin tones and matched pigment blends would be of use is the manufacture of mannequins and toys such as dolls.

Whether employed to mass-pigment plastics or in surface coatings, pigment blends that appear natural under all illuminations would produce an improved appearance over the crude pinks and browns currently employed. This approach may also be of benefit in the production of waxworks, which could then be more accurately matched to the skin tone of the subject.

The following pigments have been incorporated into the full palette database referred to above. They are referenced by CI (Color Index) numbers, together with conventional names where available.

| Blue Colorants | |
|---|---|
| CI - 74160 Phthalocyanine Blue (Cosmetic) | CI - 74100 Phthalocyanine Blue |
| CI - 69810 Indanthrone Blue | CI - 77510 Prussian Blue (Cosmetic) |
| CI - 77346 Cobalt Blue | CI - 77007 Ultramarine Blue (Cosmetic) |
| CI - 77112 Manganese Blue | CI - 77368 Cerulean Blue |
| CI - 77343 Chromium Blue | CI - 69800 Indanthrone Blue |
| CI - 42090 (Cosmetic) | |

| Red Colorants | |
|---|---|
| CI - 12420 Naphthol Red | CI - 75330 Madder Lake |
| CI - 12460 Permanent Red | CI - 12380 Naphthol Red |
| CI - 58000 Alizarin Crimson | CI - 12390 Naphthol Red |
| CI - 73312 Thioindigoid Red | CI - 77491 Mars Red (Cosmetic) |
| CI - 77202 Cadmium Red | CI - 12370 Naphthol Red |
| CI - 77201 Mercadium Red | CI - 73915 Quinacridone Magenta |
| CI - 71145 Perylene Vermilion | CI - 12485 Naphthol Red |
| CI - 71137 Perylene Red | CI - 59300 Brominated anthranthrone |
| CI - 12475 Naphthol Red | CI - 12513 Benzimidazolone Red |
| CI - 65300 Anthraquinoid Red | CI - 71155 Perylene Red |
| CI - 71130 Perylene Maroon | CI - 12467 Perylene Red |
| CI - 71140 Perylene Scarlet | CI - 71100 Perinone Red |
| CI - 56110 Iragzin DPP | CI - 56105 Irgazin DPP Scarlet |
| CI - 73905 Quinacridone Red | CI - 73907 Quinacridone Red |
| CI - 45430 (Cosmetic) | CI - 15850 (Cosmetic) |
| CI - 15850: 1 D&C Red 7 (Cosmetic) | CI - 15850: 2 (Cosmetic) |
| CI - 15585 (Cosmetic) | CI - 45170 (Cosmetic) |
| CI - 45380: 1 (Cosmetic) | CI - 45380: 2 (Cosmetic) |
| CI - 45380: 3 (Cosmetic) | CI - 45410 (Cosmetic) |
| CI - 73360 (Cosmetic) | CI - 17200 D&C Red 33 (Cosmetic) |
| CI - 15880 Deep Maroon (Cosmetic) | CI - 12085 (Cosmetic) |
| CI - 16035 D&C Red 40 (Cosmetic) | CI - 77007 Ultramarine Pink |

| Yellow Colorants | |
|---|---|
| CI - 11710 Arylide Yellow | CI - 77205 Cadmium Zinc Yellow |
| CI - 77199 Cadmium Barium Yellow | CI - 77357 Aureolin Yellow |
| CI - 77492 Mars Yellow (Cosmetic) | CI - 77788 Nickel Yellow |
| CI - 11740 Hansa Yellow | CI - 11738 Azo Yellow |
| CI - 11741 Brilliant Yellow | CI - 21108 Diazo Yellow |
| CI - 11767 Permanent Yellow | CI - 11727 Hansa Yellow |
| CI - 68420 Anthrapyrimidine Yellow | CI - 70600 Flavanthrone Yellow |
| CI - 19140 (Cosmetic) | CI - 15985 (Cosmetic) |
| CI - 47005 Quinoline Yellow (Cosmetic) | CI - 48042 Azomethine Yellow |
| CI - 56280 Isoindolinone Yellow | CI - 56284 Isoindolinone Yellow |
| CI - 11781 Benzimidazolone Yellow | CI - 13980 Benzimidazolone Yellow |
| CI - 20037 Pigment Yellow 128 | CI - 21290 Pigment Yellow 180 |
| CI - 20710 Cromophtal Yellow 3G (Pigment Yellow 93) | |
| CI - 11680 Bright Yellow (Pigment Yellow 1) | |

| Orange Colorants | |
|---|---|
| CI - 45370: 1 (Cosmetic) | CI - 45370: 2 (Cosmetic) |
| CI - 73900 Quinacridone Gold | CI - 73920 Quinacridone Deep Gold |
| CI - 77491/2 Iron Oxide Orange | |

| Green Colorants | |
|---|---|
| CI - 74260 Monastral Green | CI - 10006 Hooker's Green |
| CI - 77288 Chromium Oxide Green (Cosmetic) | CI - 77289 Viridian Green (Cosmetic) |
| CI - 77335 Cobalt Green | CI - 77009 Green Earth |
| CI - 74265 Phthalocyanine Green | CI - 77377 Light Green Oxide |

| Violet Colorants | |
|---|---|
| CI - 77007 Ultramarine Violet (Cosmetic) | CI - 77360 Cobalt Violet |
| CI - 77742 Manganese Violet (Cosmetic) | CI - 73900 Quinacridone Violet |
| CI - 51319 Dioxazine Violet | CI - 60010 Isoviolanthrone Violet |
| CI - 77015 Iron Oxide Violet | |

| White Colorants | |
|---|---|
| CI - 77891 Titanium Dioxide (Cosmetic) | CI - 77947 Zinc White (Cosmetic) |
| CI - 77115 Lithopone White | CI - 77811 Silica |
| CI - 77002 Alumina Hydrate | CI - 77004 Kaolin |
| CI - 77120 Blanc Fixe (Barytes) | |

| Black Colorants | |
|---|---|
| CI - 77266 Carbon Black | CI - 77499 Iron Oxide Black (Cosmetic) |

The currently preferred "core" pigments are as follows:

Titanium dioxide; Pigment Yellow 93; quinacridone magenta; perylene maroon; manganese violet; Mars red; Mars yellow; ultramarine pink; ultramarine blue; viridian; phthalocyanine green.

Titanium dioxide is the white pigment of choice, although zinc oxide may also be used. Pigment Yellow 93 (for example sold as Cromophtal Yellow 3G—Cromophtal is a registered trade mark of Ciba Geigy) is a bright yellow. It is technically a slightly green-shade yellow, but for practical purposes, it can be regarded as effectively mid-shade. Quinoline yellow, Pigment Yellow 1, arylide yellow, Pigment Yellow 128 and Pigment Yellow 180 would be convenient alternatives. Quinacridone magenta (Pigment Red 122: is a blue-shade red or violet-red, depending on one's terminology. D&C Red 33 (also used as Pigment Red 33) is an alternative blue-shade red or magenta, as is D&C Red 7. Deep maroon (Pigment Red 63) is a darker blue-shade red. Manganese violet can be considered as a blue-shade red or as a red-shade violet, depending on one's terminology.

The balancing pigment may be considered to modify the color balance of the basic combinations of white plus yellow plus red/violet pigments, above. Mars red and Mars yellow are two commonly-available iron oxide pigments; iron oxide oranges, browns, violets and blacks may also be added to the preferred palette in some cases. Perylene maroon is a deep red, while D&C Red 40 is a dark red-brown. Ultramarine pink is a blue-shade pink. Chemically, it is very similar to other ultramarine pigments.

The cold-toned pigments in the palettes comprise blues, greens and occasionally violet or black. Ultramarine blue may optionally be replaced with phthalocyanine blue or even Prussian blue. Viridian (hydrated chromium oxide green) and phthalocyanine green are versatile pigments for this purpose, and (anhydrous) chromium oxide green may also be used having a different opacity/color balance. Where a violet is required for a colder tone, manganese violet is usually sufficient, rather than add another violet such as ultramarine violet to the palette. Where black is required to darken a pigment blend, the exact black pigment used and its undertone are found not to be critical.

The above core pigments and alternatives should suffice for most skin color matches. A colorist may thus keep a relatively restricted stock of pigments or pigment concentrates, ordering in other pigments only when they become necessary for matching an unusual skin tone.

It has been found that while attempted matches using one white and three colored pigments can produce acceptable $\Delta E^*$ values, they will probably show significant metamerism. Matches with four colored pigments and one white pigment routinely produce $\Delta E^*$ values of 0.4 (hard even for a skilled matcher to see) and practically no metamerism.

It has been found that a pale Caucasian skin tone can in almost all cases be simulated using a pigment blend taken from the following palette:

Titanium dioxide; Pigment Yellow 93; quinacridone magenta; ultramarine pink or an iron oxide pigment; and a cold-toned pigment selected from ultramarine blue, phthalocyanine blue, viridian, phthalocyanine green, manganese violet or black.

A corresponding palette for darker Caucasian skin tones would be:

Titanium dioxide; Pigment Yellow 93; quinacridone magenta; ultramarine pink or an iron oxide pigment or perylene maroon; and a cold-toned pigment selected from ultramarine blue, phthalocyanine blue, viridian and chromium oxide green.

A corresponding palette for paler Asian skin tones would be;

Titanium dioxide; Pigment Yellow 93; perylene maroon; ultramarine pink or an iron oxide pigment; and a cold-toned pigment selected from ultramarine blue, phthalocyanine blue, viridian, phthalocyanine green and black.

For darker Asian skin tones, the corresponding preferred palette would be:

Titanium dioxide; Pigment Yellow 93; quinacridone magenta or manganese violet; ultramarine pink or perylene maroon or an iron oxide pigment; and a cold-toned pigment selected from ultramarine blue, phthalocyanine blue, viridian, chromium oxide green and black.

For lighter Afro-Caribbean skin tones, the currently preferred palette would be:

Titanium dioxide; Pigment Yellow 93; manganese violet, deep maroon or perylene maroon; ultramarine pink or an iron oxide pigment; and a cold-toned pigment selected from ultramarine blue, phthalocyanine blue, viridian, phthalocyanine green or black.

Darker Afro-Caribbean skin tones can usually be matched with a pigment blend from the following palette:

Titanium dioxide; Pigment Yellow 93; perylene maroon or manganese violet; an iron oxide pigment or ultramarine blue; and a cold-toned pigment selected from ultramarine blue, phthalocyanine blue, viridian, chromium oxide green and black (N.B. for dark Afro-Caribbean skin, a blue balancing pigment is indeed sometimes required).

While other palettes have been developed, those listed above have the advantage that the pigments used are generally readily available. For example, the pigments quinacridone gold and quinacridone deep gold are very useful in color-matching Afro-Caribbean skin tones, but have recently become almost unobtainable. This has required thorough reformulation to create fresh palettes. Since it is always possible that other pigments may in future become unavailable for production, health and safety or simply economic reasons, there will remain a need for the full color matching method described above, as well as the methods based on predetermined base formulations.

The application in which the pigments are to be used may determine the exact pigment choice. For example, quinacridone magenta is a very useful red pigment for silicones for prostheses, but for skin condition camouflage compositions, D&C Red 7 tends to be used more often instead. Similarly, Pigment Yellow 93 is an extremely useful pigment for pigmenting prostheses, but quinoline yellow tends to be more useful for skin condition camouflage.

The invention claimed is:

1. A method of matching a skin color comprising the steps of providing a color measurement device adapted to measure a first spectral reflectance curve of an area of skin to be matched, providing a colorant database containing a plurality of colorant spectral reflectance curves each for a respective one of a plurality of colorants, measuring a first spectral reflectance curve for a selected area of skin, comparing said first spectral reflectance curve to said colorant spectral reflectance curves and determining a recommended blend of colorants chosen from the colorant database, said recommended blend having a calculated spectral reflectance curve substantially corresponding to the measured first spectral reflectance curve for the selected area of skin, and recording in a formulation database a recommended blend of colorants found to constitute a successful match, together with respective spectral reflectance curves and color values for the blend.

2. A method as claimed in claim 1, comprising the further steps of preparing a sample of said recommended blend in an application medium, measuring a spectral reflectance curve of the sample and comparing the curve of the sample and the first spectral reflectance curve for the selected area of skin in order to check a match.

3. A method as claimed in claim 1, further comprising the step of providing a palette of pigments corresponding to selected ones of the colorants present in the colorant database.

4. A method of matching a skin color comprising the steps of providing a color measuring device adapted to measure color data of an area of skin to be matched, providing a formulation database containing a plurality of blends of colorants that have previously been found to match skin colors by the method as claimed in claim 1, along with respective color data for said blends, measuring color data for a selected area of skin and selecting from the formulation database a recommended blend of colorants which has calculated color data closest to the color data measured for the selected area of skin.

5. A method as claimed in claim 4, wherein said color data comprise tristimulus color values, and the colorant blend selection step comprises calculating color differences between calculated color data for blends of colorants and measured color data for the selected area of skin, according to at least one formula selected from a group comprising the $\Delta E^*$, CMC and CIE94 formulae.

6. A method as claimed in claim 4, wherein said color data comprise spectral reflectance curves.

7. A method as claimed in claim 4, comprising the further steps of determining a difference between the color data calculated for the recommended blend of colorants and the color data measured for the selected area of skin, comparing said difference with a predetermined threshold value, and when said difference exceeds the threshold value, modifying the recommended blend of colorants to reduce said difference below the threshold value.

8. A method as claimed in claim 7, wherein said modification step comprises so modifying the recommended blend of colorants using colorants selected from the colorant database that the modified recommended blend has a calculated spectral reflectance curve substantially corresponding to the first spectral reflectance curve measured for the selected area of skin.

9. A method as claimed in claim 4, also comprising the step of providing a palette of pigments corresponding to colorants used in the colorant blends present in the formulation database.

10. Apparatus for matching skin color comprising a color measurement device adapted to measure a first spectral reflectance curve for a selected area of skin and operatively linked to a first computer, the first computer being connected to a colorant database containing a plurality of reference spectral reflectance curves each for a respective one of a plurality of colorants, wherein the first computer is programmed to determine a recommended blend of colorants by combining colorant reference spectral reflectance curves substantially to match a first spectral reflectance curve of the selected area of skin.

11. Apparatus as claimed in claim 10, also comprising a plurality of samples of colorants corresponding to selected ones of those present in the colorant database.

12. Apparatus for matching skin color comprising a color measurement device adapted to measure color data for a selected area of skin and operatively linked to a first computer, the first computer being connected to a formulation database containing a plurality of blends of colorants that have previously been found to match skin colors by the method as claimed in claim 1, along with respective color data of the blends, wherein the first computer is programmed to select from the formulation database a recommended blend of colorants which has calculated color data closest to the color data measured for the selected area of skin.

13. Apparatus as claimed in claim 12, wherein said color data comprise spectral reflectance curves.

14. Apparatus as claimed in claim 12, wherein said color data comprise tristimulus color values.

15. Apparatus as claimed in claim 12, also comprising a plurality of samples of colorants corresponding to the colorants present in the blends of colorants present in the formulation database.

16. The method of matching skin colors as claimed in claim 3, wherein the palette of pigments comprises a white pigment, a first substantially yellow pigment, a first substantially red pigment, a cold-toned pigment and at least one balancing pigment.

17. The method of matching skin colors as claimed in claim 16, wherein said first substantially yellow pigment comprises a substantially mid-shade yellow pigment.

18. The method of matching skin colors as claimed in claim 17, wherein said substantially mid-shade yellow pigment is selected from a group comprising Pigment Yellow 93 (Color Index 20170), quinoline yellow (Color Index 47005), Pigment Yellow 1 (Color Index 11680), arylide yellow (Color Index 11710), Pigment Yellow 128 (Color Index 20037) and Pigment Yellow 180 (Color Index 21290).

19. The method of matching skin colors as claimed in claim 16, wherein the first substantially red pigment is a dark red pigment.

20. The method of matching skin colors as claimed in claim 16, wherein the first substantially red pigment is a blue-shade red pigment.

21. The method of matching skin colors as claimed in claim 16, wherein the first substantially red pigment is selected from a group comprising quinacridone magenta (Pigment Red 122; Color Index 73915), deep maroon (Pigment Red 63; Color Index 15880), perylene maroon (Pigment Red 179; Color Index 71130), D&C Red 7 (Color Index 15850:1), D&C Red 33 (Color Index 17200), and manganese violet (Color Index 77742).

22. The method of matching skin colors as claimed in claim 16, wherein said cold-toned pigment comprises a green pigment.

23. The method of matching skin colors as claimed in claim 22, wherein said green pigment is selected from a group comprising chromium oxide green (Color Index 77288), viridian (hydrated chromium oxide green; Color Index 77289) and phthalocyanine green (Color Index 74265).

24. The method of matching skin colors as claimed in claim 16, wherein said cold-toned pigment comprises a blue pigment.

25. The method of matching skin colors as claimed in claim 24, wherein said blue pigment is selected from a group comprising ultramarine blue (Color Index 77007), phthalocyanine blue (Color Index 74160) and Prussian blue (Color Index 77510).

26. The method of matching skin colors as claimed in claim 16, wherein said cold-toned pigment comprises a black pigment.

27. The method of matching skin colors as claimed in claim 16, wherein said cold-toned pigment comprises a violet pigment.

28. The method of matching skin colors as claimed in claim 16, wherein the at least one balancing pigment comprises an iron oxide pigment selected from a group comprising Mars yellow (Color Index 77492), Mars red (Color Index 77491), maroon red (Color Index 77491), iron oxide oranges and browns (Color Index 77491 and 77492), iron oxide violet (Color Index 77105) and iron oxide black (Color Index 77499).

29. The method of matching skin colors as claimed in claim 16, wherein the at least one balancing pigment comprises a dark red pigment selected from a group comprising perylene maroon (Color Index 71130) and D&C Red 40 (Color Index 16035).

30. The method of matching skin colors as claimed in claim 16, wherein the at least one balancing pigment comprises an ultramarine pigment selected from a group comprising ultramarine pink and ultramarine blue (both Color Index 77007).

31. A method of providing a prosthesis comprising employing material pigmented by the method as claimed in claim 1.

32. A method of providing a prosthesis comprising employing material pigmented by the method as claimed in claim 16.

33. A method of providing a skin condition camouflage composition comprising employing material pigmented by the method as claimed in claim 1.

34. A method of providing a skin condition camouflage composition comprising employing material pigmented by the method as claimed in claim 16.

35. A method as claimed in claim 5, wherein said tristimulus color values are expressed according to a system selected from a group comprising the CIE L*a*b* and CIE L*c*h° systems.

* * * * *